(12) United States Patent
Failli et al.

(10) Patent No.: US 6,340,687 B1
(45) Date of Patent: Jan. 22, 2002

(54) SUBSTITUTED TETRAHYDRO-PYRIMIDINE-2(1H)-THIONE HDL-C ELEVATORS USEFUL AS ANTIATHEROSCLEROTIC AGENTS

(75) Inventors: Amedeo A. Failli, Princeton Junction; Jay S. Shumsky, Hightstown; Kevin A. Memoli, Cranbury, all of NJ (US); Donald P. Strike, St. Davids, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/145,895

(22) Filed: Sep. 2, 1998

Related U.S. Application Data

(60) Provisional application No. 60/056,308, filed on Sep. 3, 1997.

(51) Int. Cl.[7] .................... C07D 239/40; A61K 31/513
(52) U.S. Cl. ........................ 514/274; 544/315
(58) Field of Search ............. 544/315; 514/274

(56) References Cited

U.S. PATENT DOCUMENTS 2,662,080 A * 12/1953 Smith .................... 260/250
5,276,049 A * 1/1994 Himmelsbach et al. ..... 514/392

FOREIGN PATENT DOCUMENTS

| EP | 0503548 | 9/1992 |
| EP | 0612741 | 8/1994 |
| JP | 3176475 | 7/1991 |

OTHER PUBLICATIONS

Russ et al., *Am. J. Med.*, 11:480–493 (1951).
Gofman et al., *Circulation*, 34:679–697 (1966).
Miller and Miller, *Lancet*, 1:16–19 (1975).
Gordon et al., *Circulation*, 79:8–15 (1989).
Stampfer et al., *N. England J. Med.*, 325:373–381 (1991).
Badimon et al., *Lab. Invest . . .* , 60:455–461 (1989).
Miller et al., *Br. Med. J.*, 282:1741–1744 (1981).
Picardo et al., *Atreriosclerosis.*, 6:434–441 (1986).
Glomset, *J. Lipid Res.*, 9:155–167 (1968).
Glass et al., *J. Biol. Chem.*, 258:7161–7167 (1983).
MacKinnon et al., *J. Biol. Chem.*, 261:2548–2552 (1986).
Grow and Fried, *J. Biol. Chem.*, 253:1834–1841 (1978).
Lagocki and Scanu., *J. Biol. Chem.*, 255:3701–3706 (1980).
Schaefer et al., *J. Lipid Res . . .* , 23:1259–1273 (1982).
Kashima, C. et al., *J. Chem. Soc. Perkin, I.*, 6:1622–1625 (1981).
Sondhi, S. M. et al., *Synthesis*, 1175–1180 (1994).
Sondhi, S. M. et al., *Indian Drugs*, 31(7):317–320 (1994).
Chicault, M. et al., *Arzneim.–Forsch.*, 40:55–57 (1990).
Moskovkin, A. S., *Farmakol. Toksiko. (Moscow)*, 41:494–497 (1978). Consider structures only.
Kumanova, B. K., *Dokl. Bolg. Akad. Nauk.*, 35:49–51 (1982).
Moskovkin, A. S. et al., *Khim. Gerotsikl. Soedin.*, 1273–1278 (1983). Consider structures only.
Unkovskii, B. V. et al., *Khim. Gerotsikl. Soedin.*, 889–895 (1969). Consider CAPLUS abstract only.

\* cited by examiner

*Primary Examiner*—John M. Ford
(74) *Attorney, Agent, or Firm*—Michael R. Nagy

(57) ABSTRACT

Antiatherosclerotic agents are provided having the following structure:

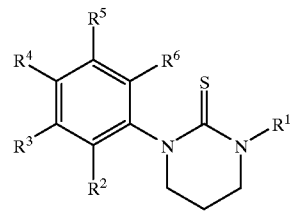

wherein:

$R^1$ is hydrogen, alkyl of 1–6 carbon atoms, cycloalkyl of 3–8 carbon atoms, alkenyl of 2–7 carbon atoms, alkynyl of 2–7 carbon atoms, or phenylalkyl of 7–10 carbon atoms; and $R^2$, $R^3$, $R^4$, $R^5$, and $R^6$ are each, independently, hydrogen, halogen, alkyl of 1–6 carbon atoms, cycloalkyl of 3–8 carbon atoms, alkenyl of 2–7 carbon atoms, alkynyl of 2–7 carbon atoms, aralkyl of 7–10 carbon atoms, alkoxy of 1–6 carbon atoms, aryloxy of 6–12 carbon atoms, aralkyloxy of 7–12 carbon atoms, fluoroalkoxy of 1–6 carbon atoms, trifluoromethyl, alkylthio of 1–3 carbon atoms, alkylsulfonyl of 1–3 carbon atoms, —$SCF_3$, nitro, alkylamino in which the alkylamino moiety has 1–6 carbon atoms, or dialkylamino in which each alkyl group has 1–6 carbon atoms; or a pharmaceutically acceptable salt thereof.

23 Claims, No Drawings

SUBSTITUTED TETRAHYDRO-PYRIMIDINE-2(1H)-THIONE HDL-C ELEVATORS USEFUL AS ANTIATHEROSCLEROTIC AGENTS

This application claims the benefit of U.S. Provisional Application No. 60/056,308, filed Sep. 3, 1997.

FIELD OF THE INVENTION

This invention is directed to anti-atherosclerotic agents and more specifically to compounds, compositions and methods for treating atherosclerotic conditions such as dyslipoproteinimias and coronary heart disease. This invention specifically relates to substituted tetrahydro-pyrimidine-2 (1H)-thione derivatives that elevate HDL cholesterol (HDL-C) concentration and which may be useful for the treatment of atherosclerotic conditions and coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.*, 11, 480–483 (1951); Gofman et al., *Circulation*, 34, 679–697 (1966); Miller and Miller, *Lancet*, 1, 16–19 (1975); Gordon et al., *Circulation*, 79, 8–15 (1989); Stampfer et al., *N. Engl. J. Med.* 325, 373–381 (1991); Badimon et al., *Lab. Invest.*, 60, 455–461 (1989)). Atherosclerosis is the process of the accumulation of cholesterol within the arterial wall which results in the occlusion, or stenosis, of coronary and cerebral arterial vessels and subsequent myocardial infarction and stroke. Angiographic studies have shown that elevated levels of some HDL particles in humans appear to be correlated to a decreased number of sites of stenosis in the coronary arteries of humans (Miller et al., *Br. Med. J.*, 282, 1741–1744 (1981)).

There are several mechanisms by which HDL may protect against the progression of atherosclerosis. Studies in vitro have shown that HDL is capable of removing cholesterol from cells (Picardo et al., *Arteriosclerosis*, 6, 434–441 (1986)). Data of this nature suggest that one antiatherogenic property of HDL may lie in its ability to deplete tissue of excess free cholesterol and eventually lead to the delivery of this cholesterol to the liver (Glomset, *J. Lipid Res.*, 9, 155–167 (1968)). This has been supported by experiments showing efficient transfer of cholesterol from HDL to the liver (Glass et al., *J. Biol. Chem.*, 258 7161–7167 (1983); McKinnon et al., *J. Biol. Chem.*, 26, 2548–2552 (1986)). In addition, HDL may serve as a reservoir in the circulation for apoproteins necessary for the rapid metabolism of triglyceride-rich lipoproteins (Grow and Fried, *J. Biol. Chem.*, 253, 1834–1841 (1978); Lagocki and Scanu, *J. Biol. Chem.*, 255, 3701–3706 (1980); Schaefer et al., *J. Lipid Res.*, 23, 1259–1273 (1982)). Accordingly, agents which increase HDL cholesterol concentrations would be of utility as antiatherosclerotic agents, useful particularly in the treatment of dyslipoproteinimias and coronary heart disease.

Cyclic ureas and thioureas have heretofore been used for various purposes, all of which are unrelated to their anti-atherosclerotic effects.

For example, JP 3-176475 discloses the preparation of cyclic ureas and thioureas such as 1,3-disubstituted tetrahydro-pyrimidine-2-thiones and their use as herbicidal agents. European Patent Application Publication Nos. 0612741 and 0503548 disclose cyclic urea (thiourea) derivatives useful as aggregation inhibitors and inhibitors of cell-cell and cell-matrix interactions, respectively.

The *J. Chem. Soc. Perkin I*, 6, 1622–1625 (1981) describes the regioselective preparation of 3,4-dihydro and 3,4,5,6-tetrahydro-pyrimidine-2(1H)-ones and the corresponding thiones useful as intermediates in the synthesis of diamines, thiazines and pyrimidine-2(1H)-ones. *Synthesis*, 1175–1180 (1994) describes the synthesis of antiinflammatory pyrimidobenzimidazoles from 1-aryl-6-hydroxy-tetrahydro-pyrimidine-2-(1H)-thiones.

The use of 6-hydroxy-tetrahydro-pyrimidine-2(1H)-thiones as antiamoebic and antihelmintic agents is disclosed in *Indian Drugs*, 31, 317–320 (1994). Other uses of similar compounds are disclosed in, e.g., *Arzneim.-Forsch.*, 40, 55–57 (1990) (1-phenyl-tetrahydro-pyrimidine-2(1H)-thione as immunomodulator agents); and *Farmakol. Toksikol.* (Moscow), 41, 494–497 (1978) (1-substituted 4-hydroxy-hexahydro-pyrimidine-2-thione derivatives as radioprotectors). The production of similar thione derivatives, without reference to a specific utility has been disclosed in *Dokl. Bolg. Akad. Nauk.*, 35, 49–51 (1982) (the mass spectra of 1-substituted 2-oxo (or 2-thio) hexahydropyrimidines); *Khim. Gerotsikl. Soedin.*, 1273–1278 (1983) (the mass spectra of 1-substituted 4-hydroxy-hexahydro-pyrimidine-2-thiones; and *Khim. Gerotsikl. Soedin.*, 889–895 (1989) (the synthesis of 4-hydroxy-hexahydro-pyrimidine-2-thiones). None of these references disclose the use of cyclic ureas and thioureas to raise the HDL cholesterol concentrations in mammals.

SUMMARY OF THE INVENTION

In accordance with this invention, there are provided 1-(aryl-substituted)-3-substituted tetrahydro-pyrimidine-2 (1H)-thiones which are useful as antiatherosclerotic agents.

More particularly, this invention provides antiatherosclerotic agents of Formula 1 having the following structure:

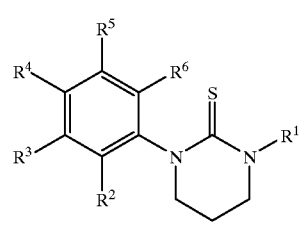

wherein
R$^1$ is hydrogen, alkyl of 1–6 carbon atoms, cycloalkyl of 3–8 carbon atoms, alkenyl of 2–7 carbon atoms, alkynyl of 2–7 carbon atoms, or phenylalkyl of 7–10 carbon atoms; and R$^2$, R$^3$, R$^4$, R$^5$, and R$^6$ are each, independently, hydrogen, halogen, alkyl of 1–6 carbon atoms, cycloalkyl of 3–8 carbon atoms, alkenyl of 2–7 carbon atoms, alkynyl of 2–7 carbon atoms, aralkyl of 7–10 carbon atoms, alkoxy of 1–6 carbon atoms, aryloxy of 6–12 carbon atoms, aralkyloxy of 7–12 carbon atoms, fluoroalkoxy of 1–6 carbon atoms, trifluoromethyl, alkylthio of 1–3 carbon atoms, alkylsulfonyl of 1–3 carbon atoms, —SCF$_3$, nitro, alkylamino in which the alkylamino moiety has 1–6 carbon atoms, or dialkylamino in which each alkyl group has 1–6 carbon atoms;
or a pharmaceutically acceptable salt thereof.

This invention also provides methods of elevating the HDL concentration and treating or inhibiting atherosclerosis and related coronary heart disease, or dyslipoproteinemias, and improving the HDL/LDL cholesterol ratio in a mammal in need thereof which comprises administering to the mammal a compound of Formula 1 having the structure:

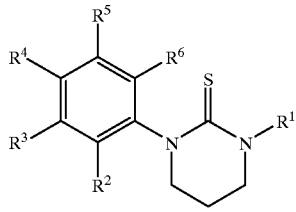

1 wherein
R$^1$ is hydrogen, alky of 1–6 carbon atoms, cycloalkyl of 3–8 carbon atoms, alkenyl of 2–7 carbon atoms, alkynyl of 2–7 carbon atoms, or phenylalkyl of 7–10 carbon atoms; and
R$^2$, R$^3$, R$^4$, R$^5$, and R$^6$ are each, independently, hydrogen, halogen, alkyl of 1–6 carbon atoms, cycloalkyl of 3–8 carbon atoms, alkenyl of 2–7 carbon atoms, alkynyl of 2–7 carbon atoms, aralkyl of 7–10 carbon atoms, alkoxy of 1–6 carbon atoms, aryloxy of 6–12 carbon atoms, aralkyloxy of 7–12 carbon atoms, fluoroalkoxy of 1–6 carbon atoms, trifluoromethyl, alkylthio of 1–3 carbon atoms, alkylsulfonyl of 1–3 carbon atoms, —SCF$_3$, nitro, alkylamino in which the alkylamino moiety has 1–6 carbon atoms, or dialkylamino in which each alkyl group has 1–6 carbon atoms;
or a pharmaceutically acceptable salt thereof.

DETAILED DESCRIPTION OF THE INVENTION

It is preferred that the compounds of the present invention are represented by the compounds of Formula 1 where R$^1$ is alkyl of 1–6 carbon atoms, alkenyl of 2–7 carbon atoms or cycloalkyl of 3–8 carbon atoms; and R$^2$, R$^3$, R$^4$, R$^5$, and R$^6$ are each, independently, hydrogen, halogen or alkyl of 1–6 carbon atoms.

More preferably, the compounds of the present invention are represented by the compounds of Formula 1 where R$^1$ is methyl, ethyl, isopropyl or cyclobutyl; and R$^2$, R$^3$, R$^4$, R$^5$, and R$^6$ are each, independently, chlorine or methyl.

As used in describing this invention, the terms "alkyl", "alkenyl", and "alkynyl" include both straight chain as well as branched moieties. This includes the alkyl portions of substituents such as alkoxy, thioalkyl, alkylsulfinyl, alkylsulfonyl, fluoroalkoxy, and the like. The terms "halo" and "halogen" include fluorine, chlorine, bromine, and iodine. Fluoroalkoxy includes mono-, di-, tri-, and polyfluorinated alkoxy moieties, such as —OCF$_3$, —OCH$_2$F, —OCHF$_2$, —OCH$_2$CF$_3$, and the like. The term "aryl" includes radicals such as benzyl, phenyl or naphthyl.

As used in describing this invention, the term "compounds of this invention" includes the broader description encompassing the formula used in accordance with the above methods, as well as the narrower description encompassing the formula used in accordance with the above novel compounds.

The pharmaceutically acceptable salts of the compounds of this invention are those derived from organic and inorganic acids such as, but not limited to: acetic, lactic, citric, tartaric, succinic, fumaric, maleic, malonic, mandelic, malic, hydrochloric, hydrobromic, phosphoric, nitric, sulfuric, methane sulfonic, toluene sulfonic and similarly known acceptable acids.

The most preferred compounds of the present invention are:

1-(4-chloro-2-methyl-phenyl)-3,4,5,6-tetrahydro-pyrimidine-2(1H)-thione;
1-phenyl-3,4,5,6-tetrahydro-pyrimidine-2(1H)-thione;
1-(4-chloro-2-methyl-phenyl)-3-ethyl-3,4,5,6-tetrahydro-pyrimidine-2(1H)-thione;
1-(2,6-dimethyl-phenyl)-3,4,5,6-tetrahydro-pyrimidine-2(1H)-thione;
1-(5-chloro-2-methyl-phenyl)-3-ethyl-3,4,5,6-tetrahydro-pyrimidine-2(1H)-thione;
1-(5-chloro-2-methyl-phenyl)-3-isopropyl-3,4,5,6-tetrahydro-pyrimidine-2(1H)-thione;
1-(4-chloro-2-methyl-phenyl)-3-isopropyl-3,4,5,6-tetrahydro-pyrimidine-2(1H)-thione;
3-allyl-1-(5-chloro-2-methyl-phenyl)-3,4,5,6-tetrahydro-pyrimidine-2(1H)-thione;
1-(5-chloro-2-methyl-phenyl)-3-methyl-3,4,5,6-tetrahydro-pyrimidine-2(1H)-thione;
3-allyl-1-(4-chloro-2-methyl-phenyl)-3,4,5,6-tetrahydro-pyrimidine-2(1H)-thione;
1-(4-chloro-2-methyl-phenyl)-3-methyl-3,4,5,6-tetrahydro-pyrimidine-2(1H)-thione;
3-allyl-1-(6-chloro-2-methyl-phenyl)-3,4,5,6-tetrahydro-pyrimidine-2(1H)-thione;
1-(6-chloro-2-methyl-phenyl)-3-methyl-3,4,5,6-tetrahydro-pyrimidine-2(1H)-thione;
1-(5-chloro-2-methyl-phenyl)-3-isobutyl-3,4,5,6-tetrahydro-pyrimidine-2(1 H)-thione;
1-(6-chloro-2-methyl-phenyl)-3-isopropyl-3,4,5,6-tetrahydro-pyrimidine-2(1H)-thione;
1-(6-chloro-2-methyl-phenyl)-3-ethyl-3,4,5,6-tetrahydro-pyrimidine-2(1H)-thione;
1-(4-chloro-2-methyl-phenyl)-3-isobutyl-3,4,5,6-tetrahydro-pyriniidine-2(1H)-thione;
1-(6-chloro-2-methyl-phenyl)-3-cyclobutyl-3,4,5,6-tetrahydro-pyrimidine-2(1H)-thione;
1-(5-chloro-2-methyl-phenyl)-3-cyclobutyl-3,4,5,6-tetrahydro-pyrimidine-2(1H)-thione; and
1-(6-chloro-2-methyl-phenyl)-3-isobutyl-3,4,5,6-tetrahydro-pyrimidine-2(1H)-thione.

The 1-(aryl-substituted)-3-substituted-tetrahydro-pyrimidine-2(1H)-thiones of this invention may be prepared by cyclocondensation of an appropriately substituted diamine of formula (2) with a thiocarbonylating agent as shown in Scheme 1.

Scheme 1

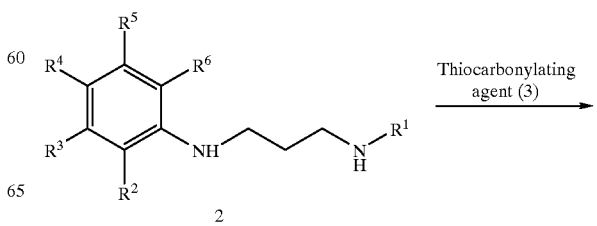

2

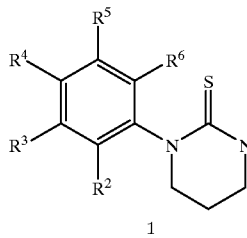

1 wherein $R^1$, $R^2$, $R^3$, $R^4$, $R^5$, and $R^6$ are as described above for Formula 1.

The thiocarbonylation agent (3) of Scheme 1 may be thiophosgene in an organic aprotic solvent, such as dichloromethane or chloroform, in the presence of an organic base such as triethylamine, at temperatures ranging from 0° C. to ambient essentially according to the method of Sharma et al., *J. Med. Chem.*, 18, 913 (1975) (for a review of thiophosgene in organic syntheses see Sharma, *Synthesis*, 803 (1978)).

Alternatively, the cyclocondensation can be carried out with a heterocyclic thiocarbonyl transfer reagent (3) such as 1,1'-thiocarbonyldiimidazole (as disclosed in Staab et al., *Angew. Chemie*, 73, 148 (1961); Staab et al., *Justus Liebigs Ann. Chem.*, 657, 98 (1962); and Larsen et al., *J. Org. Chem.*, 43, 337 (1978)), or 1,1'-thiocarbonyl-di-1,2,4-triazole (as disclosed in Larsen et al., *J. Org. Chem.*, 43, 337 (1978)) in an organic aprotic solvent such as dichloromethane or dioxane at temperatures ranging from ambient to the reflux temperature of the solvent.

It is generally accepted that the cyclocondensation proceeds through the intermediacy of an heterocyclic N-thiocarboxamide such as imidazole- or 1,2,4-triazole-N-thiocarboxamide of general formula (4) as shown in Scheme 2 (Staab, *Angew. Chemie Int. Ed.*, 1, 351 (1962)). It has been found that cyclocondensation of the intermediate (4) to the desired tetrahydro-pyrimidine-2(1H)-thiones of formula (1) can be accelerated by the addition of an organic acid (5) such as para-toluene sulfonic acid monohydrate to the reaction mixture containing the intermediate N-thiocarboxamide of formula (3).

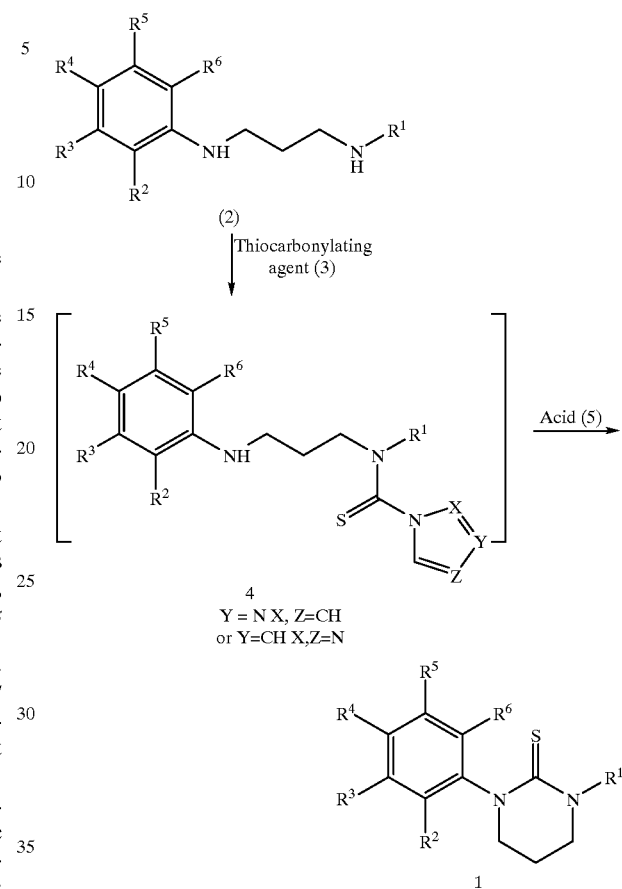

Scheme 2 wherein $R^1$, $R^2$, $R^3$, $R^4$, $R^5$, and $R^6$ are as described above for Formula 1.

The intermediate substituted diamines of general formula (2) of Schemes 1 and 2 can be prepared by either one of the two routes shown in Scheme 3.

SCHEME 3

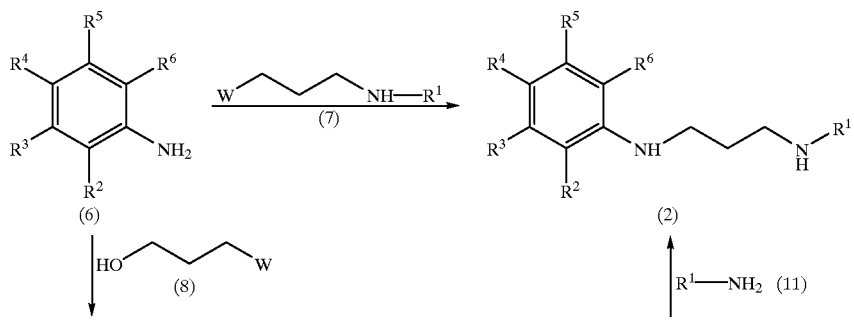

-continued

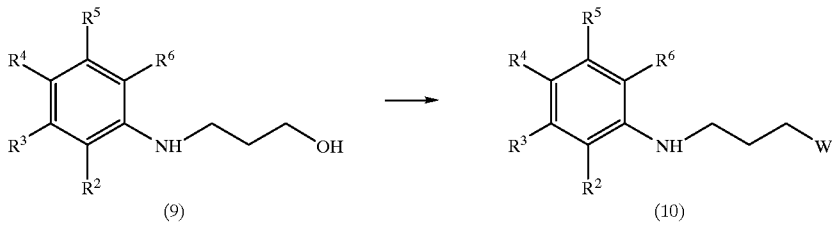

Thus, an appropriately substituted aniline of general formula (6) can be alkylated with a haloalkylamine, preferably a bromo(chloro)alkylamine of formula (7, W=Br, Cl), in the absence of a solvent and at temperatures ranging from ambient to the reflux temperature of the aniline employed, to provide the desired diamines of Formula (2) of Schemes 1 and 2.

Alternatively, the aniline of formula (6) is first allylated with a haloalkanol, preferably a bromo(chloro)alkanol of general formula (8, W=Br, Cl), to provide the intermediate aminoalkanol of formula (9) which is in turn converted to the haloalkylamine intermediate of formula (10, W=Br, Cl). Reaction of (10) with an amine of formula (11) yields the desired diamines of formula (2) of Schemes 1 and 2, wherein $R^1$, $R^2$, $R^3$, $R^4$, $R^5$, and $R^6$ are as described above for formula 1.

The appropriately substituted aniline starting materials (6) of Scheme 3 are either available commercially or can be prepared by procedures analogous to those in the literature for known compounds (see, e.g., J. March, *Advanced Organic Chemistry*, 3rd Ed., Wiley-Interscience, NY, page 1153).

The preferred bromo(chloro)alkylamines of formula (7) of Scheme 3 can be obtained by halogenation of the corresponding aminoalkanols of formula (12) as shown in Scheme 4 (see, Angiolini et al., *Gazz. Chim. Ital.*, 106, 111 (1976); Crabb et al., *Tetrahedron*, 26, 3941 (1970); Deady et al., *J. Chem. Soc. Perkin I*, 782 (1973); Deady et al., *J. Org. Chem.*, 28, 511 (1963); Sammes et al., *J. Chem. Soc. Perkin I*, 2415 (1984)).

Scheme 4

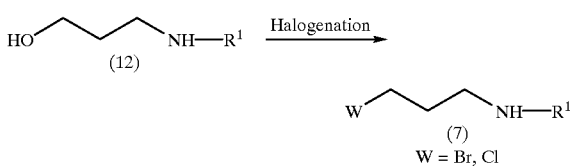

The preferred aminoalkanols of formula (12) of Scheme 4 are either available commercially or can be prepared by procedures analogous to those in the literature for known compounds (see, e.g., Will et al., *Annalen*, 568, 34 (1950); Elderfield et al., *J. Am. Chem. Soc.*, 68, 1579 (1946); Angiolini et al., *Gazz. Chim. Ital.*, 106, 111 (1976); Jones et al., *J. Chem. Soc.* (B), 1300 (1971)).

The preferred bromo(chloro)alkanols of formula (8) of Scheme 3 are either available commercially or are known in the art.

Representative compounds of this invention were evaluated in an in vivo standard pharmacological test procedure which measured the ability of the compounds of this invention to elevate HDL cholesterol levels. The following briefly describes the procedure used and results obtained. Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance was administered to a group of six rats fed the same diet with the test diet mixed in as 0.005–0.1% of the total diet. Body weight and food consumption were recorded prior to diet administration and at termination. Typical doses of the test substances were 5–100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitutiton with water the reagent contains 300 U/l cholesterol oxidase, 100 U/l cholesterol esterase, 1000 U/l horse radish peroxidase, 0.3 mmol/l 4-aminoantipyrine and 30.0 mmol/l p-hydroxybenzene sulfonate in a pH 6.5 buffer. In the reaction cholesterol was oxidized to produce hydrogen peroxide which was used to form a quinoneimine dye. The concentration of dye formed was measured spectrophotometrically by absorbance at 490 nm after incubation at 25° C. for 30 minutes. The concentration of cholesterol was determined for each serum sample relative to a commercial standard from Sigma.

HDL cholesterol concentrations in serum were determined by separation of lipoprotein classes by fast protein liquid chromatography (FPLC) by a modification of the method of Kieft et al., (*J. Lipid Res.*, 32, 859–866 (1991). Using this methodology, 25 mL of serum was injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 mL/min. The eluted sample was mixed on line with Boehringer-Mannheim cholesterol reagent pumped at 0.2 mL/min. The combined eluents were mixed and incubated on line through a knitted coil (Applied Biosciences) maintained at a temperature of 45° C. The eluent was monitored by measuring absorbance at 490 nm and gives a continuous absorbance signal proportional to the cholesterol concentration. The relative concentration for each lipoprotein class was calculated as the percent of total absorbance. HDL cholesterol concentration in serum was calculated as the percent of total cholesterol as determined by FPLC multiplied by the total serum cholesterol concentration.

The results obtained in this standard pharmaceutical test procedure are shown below in Table 1. In Examples 5–7, 9, 10 and 12–20 the test compounds were administered at a dose of 100 mg/kg. In Examples 1, 2, 3 and 11, the test compounds were administered at a dose of 50 mg/kg. In Example 4, the test compound was administered at a dose of 46 mg/kg and in Example 8 at a dose of 90 mg/kg. The duration of treatment for all examples was eight days.

Table I

TABLE I

| Compound of Example | HDL Cholesterol Level Increase (%) |
| --- | --- |
| Example 1 | 86 |
| Example 2 | 20 |
| Example 3 | 151.5 |
| Example 4 | 34 |
| Example 5 | 183 |
| Example 6 | 137 |
| Example 7 | 92 |
| Example 8 | 21 |
| Example 9 | 143 |
| Example 10 | 57 |
| Example 11 | 86 |
| Example 12 | 19 |
| Example 13 | 81 |
| Example 14 | 66 |
| Example 15 | 86 |
| Example 16 | 85 |
| Example 17 | 12 |
| Example 18 | 42 |
| Example 19 | 37 |
| Example 20 | 24 |

The results set forth in Table I demonstrate that the compounds of this invention are useful in raising the concentration of HDL cholesterol. Therefore, the compounds of this invention are useful for treating or inhibiting atherosclerosis, related cardiovascular disease, or dyslipoproteinemias, and for improving the HDL/LDL cholesterol ratio, and several metabolic conditions associated with low concentrations of HDL such as low HDL-cholesterol levels in the absence of dyslipidemia, metabolic syndrome, non-insulin dependent diabetes mellitus (NIDDM), familial combined hyperlipidemia, familial hypertriglyceridemia, and dyslipidemia in peripheral vascular disease (PVD).

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g. as tablets or capsules. In such form, the compositions may be sub-divided in unit doses containing appropriate quantities of the present compounds. The unit dosage forms can be packaged compositions, for example packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The following non-limiting examples illustrate the preparation of representative compounds of this invention.

EXAMPLE 1

1-(4-Chloro-2-methyl-phenyl)-3,4,5,6-tetrahydro-pyrimidine-2(1H)-thione

Step A. N-(4-Chloro-2-methyl-phenyl)-propane-1,3-diamine

A mixture of 4-chloro-2-methylaniline (8 g) and 3-bromopropylamine hydrobromide (5 g) was heated at 100° C. for fifteen minutes. After cooling to room temperature, the resulting crystalline solid was dissolved in water (50 mL) and one equivalent of sodium hydroxide was added. This solution was then washed with ethyl ether and basified with excess sodium hydroxide. It was then extracted with dichloromethane, the combined extracts were dried over anhydrous potassium carbonate and evaporated to dryness.

The resulting diamine was obtained as an amber oil (4.2 g, 93%) which was used as such in the next step.

$^1$H NMR (300 MHz, CDCl$_3$) δ7.1 (m, 2H), 6.5 (d, 1H), 3.2 (t, 2H), 2.9 (t, 2H), 2.1 (s, 3H), 1.8 (quiny, 2H).

Step B. 1-(4-Chloro-2-methyl-phenyl)-3,4,5,6-tetrahydro-pyrimidine-2(1H)-thione

The diamine of Step A and one equivalent of 1,1'-thiocarbonyldiimidazole were dissolved in dioxane (20 mL)

and refluxed under nitrogen for one hour. The solvent was then removed and the residue triturated with ethyl ether/ethyl acetate. The solid was filtered and washed with ethyl ether to provide the title compound (4.2 g, 83%) as an off-white solid, m.p. 266–268° C.

Anal. Calcd. for $C_{11}H_{13}ClN_2S$: C, 54.88; H, 5.44, N, 11.69. Found: C, 54.45; H, 5.28; N, 11.46.

EXAMPLE 2

1-Phenyl-3,4,5,6-tetrahydro-pyrimidine-2(1H)-thione

Step A. N-Phenyl-propane-1,3-diamine

Prepared in the manner of Example 1, Step A from aniline and 3-bromopropylamine hydrobromide salt.

Step B. 1-Phenyl-3,4,5,6-tetrahydro-pyrimidine-2(1H)-thione

Prepared in the manner of Example 1, Step B from N-phenyl-propane-1,3-diamine of Step A and 1,1'-thiocarbonyldiimidazole, except that the cyclization was effected in dichloromethane. Workup consisted of washing with water, drying over magnesium sulfate, filtration and removal of solvent in vacuo. Purfication by flash chromatography on silica gel Merck-60 eluting with 1% methanol in dichloromethane followed by trituration with ethyl ether to provide the title compound as a white solid (2.74 g, 78%), m.p: 211–212° C., identical to the material described by Kashima et al., *J. Chem. Soc. Perkin I*, 1622 (1981).

Anal. Calc. for $C_{10}H_{12}N_2S$: C, 62.46; H, 6.29; N, 14.57. Found C, 61.88; H, 6.19; N, 14.44.

EXAMPLE 3

1-(4-Chloro-2-methyl-phenyl)-3-ethyl-3,4,5,6-tetrahydro-pyrimidine-2(1H)-thione

Step A. N-Acetyl-1-amino-3-hydroxy-propane

1-Amino-3-hydroxy-propane (25 g) dissolved in methyl acetate (200 mL) was refluxed under nitrogen for three days. The methyl acetate was removed in vacuo, the residue was redissolved in toluene (100 mL) and refluxed for two days. The bottom layer containing the product was separated and the residual toluene removed in vacuo to provide the intermediate N-acetyl-1-amino-3-hydroxy-propane as a yellow liquid (36.3 g, 93%) which was used as such in the next step.

Step B. N-Ethyl-1-amino-3-hydroxy-propane

To a stirred suspension of lithium aluminum hydride (16.3 g) in dry tetrahydrofuran (300 mL) was added dropwise a solution of N-acetyl-1-amino-3-hydroxy-propane (25.2 g) of Step A in tetrahydrofuran (100 mL) over 30 minutes. The reaction mixture was then refluxed under nitrogen for 48 hours, cooled to room temperature, diluted with dichloromethane (400 mL) and quenched by the careful addition of water (31 mL) followed by 2.5 N sodium hydroxide (58 mL). The mixture was filtered through Celite and the solvent removed in vacuo to provide the intermediate N-ethyl-1-amino-3-hydroxy-propane as an orange liquid (19.5 g, 88%) which was used as such in the next step.

Step C. N-ethyl-1-amino-3-bromopropane 1:1 salt with hydrobromic acid

The N-ethyl-1-amino-3-hydroxy-propane (19.5 g) of Step B was dissolved in 48% hydrobromic acid (200 mL) and the solution was refluxed under nitrogen for 2 hours. The reaction mixture was then cooled and the hydrobromic acid was removed in vacuo. The dark residue was dissolved in dichloromethane and filtered through magnesium sulfate. The solvent was then removed and the residue was crystallized from 10% acetonitrile in ethyl acetate to provide the title hydrobromide salt as an off-white crystalline solid (22.97 g, 49%), m.p. 141–143° C.

Anal. Calcd. for $C_5H_{12}BrN$: C, 24.32; H, 5.31; N, 5.67. Found: C, 24.40; H, 5.42; N, 5.74.

Step D. N'-(4-Chloro-2-methyl-phenyl)-N-ethyl-propane-1,3-diamine

Prepared in the manner of Example 1, Step A using 2-methyl-4-chloroaniline and the N-ethyl-1-amino-3-bromopropane hydrobromide salt of Step C (12.7 g).

Step E. 1-(4-Chloro-2-methyl-phenyl)-3-ethyl-3,4,5,6-tetrahydro-primidine-2(1H)-thione The cyclization of the crude diamine of Step D was carried out with one equivalent of 1,1'-thiocarbonyldiimidazole in refluxing dioxane under nitrogen for one hour. Subsequently, two equivalents of para-toluenesulfonic acid hydrate were added and the mixture was refluxed for 48 hours. The solvent was removed in vacuo and the residue was dissolved in dichloromethane (100 mL). The solution was washed with water, dried over magnesium sulfate, filtered and evaporated. The crude product was purified by flash chromatography (on Merck-60 silica gel) eluting with 10–25% petroleum ether/ethyl acetate. The title compound was obtained as a white solid (4.4 g, 52%), m.p. 116–118° C.

Anal. Calcd. for $C_{13}H_{17}ClN_2S$: C, 58.09; H, 6.37; N, 10.42. Found: C, 58.24; H, 6.39; N, 10.32.

EXAMPLE 4

1-(2,6-Dimethyl-phenyl)-3,4,5,6-tetrahydro-pyrimidine-2(1H)-thione

Step A. N-(2,6-Dimethyl-phenyl)-propane-1,3-diamine

Prepared in the manner of Example 1, Step A except that 2,6-dimethylaniline was used as the amine.

Step B. 1-(2,6-Dimethyl-phenyl)-3,4,5,6-tetrahydro-pyrimidine-2(1H)-thione

Prepared in 22% yield in the manner of Example 1, Step B from the diamine of Step A above except that dichloromethane was used as the solvent for the cyclization. The reaction mixture was cooled, washed with water, dried over magnesium sulfate, filtered and the solvent removed in vacuo to yield the title compound as a white solid, m.p. 249–251° C.

Calcd. for $C_{12}H_{16}N_2S$: C, 65.41; H, 7.32; N, 12.71 Found: C, 64.55; H, 7.36; N, 12.58.

EXAMPLE 5

1-(5-Chloro-2-methyl-phenyl)-3-ethyl-3,4,5,6-tetrahydro-pyrimidine-2(1H)-thione

Step A. N'-(5-Chloro-2-methyl-phenyl)-N-ethyl-propane-1,3-diamine

A mixture of 5-chloro-2-methylaniline (12.3 g) and the N-ethyl-1-amino-3-bromopropane hydrobromide salt of Example 3, Step C (8.6 g) was heated at 100° C. under nitrogen for 20 minutes. After cooling, a solid mass formed which was partitioned between dichloromethane and 1 N sodium hydroxide. The organic phase was washed with brine, dried over anhydrous potassium carbonate, filtered and concentrated in vacuo to give a brown oil. The crude material was dissolved in dichloromethane and absorbed onto a column of Merck-60 flash silica gel. Elution with a solvent gradient (from 100% dichloromethane to 9:1 dichloromethane-methanol containing 0.2% ammonium hydroxide) provided the title compound (7.3 g, 92.8%) as a brown oil, which was used as such in the next step.

$^1$H NMR (DMSO-$d_6$, 400 MHz): δ1.01 (t, 3H), 1.66–1.73 (m, 2H), 2.02 (s, 3H), 2.51 (q, 2H), 2.60 (t, 2H), 3.07–3.12 (m, 2H), 5.62–5.65 (m, 1H), 6.45–6.47 (m, 2H), 6.90–6.92 (m, 1H)

MS [EI, m/z]: 226 [M]$^+$.

Step B. 1-(5-Chloro-2-methyl-phenyl)-3-ethyl-3,4,5, 6-tetrahydro-pyrimidine-2(1H)-thione A solution of the diamine of Step A (7.1 g) in dioxane (250 mL) and 1,1'-thiocarbonyldiimidazole (5.6 g) was refluxed under nitrogen for 2.5 hrs. Following the addition of para-toluenesulfonic acid monohydrate (11.9 g), the reaction mixture was heated at reflux for 48 hrs. The reaction was cooled and filtered and the filtrate was concentrated in vacuo to give a brown oil. The crude material was dissolved in dichloromethane and absorbed onto a column of Merck-60 flash silica gel. Elution with 20% ethyl acetate in hexane provided a brown solid which was triturated with diethyl ether to give the title product (2.1 g, 25.0%) as a white solid, m.p. 111–112° C.

$^1$H NMR (DMSO-$d_6$, 400 MHz): δ1.13 (t, 3H), 1.97–2.10 (m, 2H), 2.12 (s, 3H), 3.33–3.58 (m, 4H), 3.86 (q, 2H), 7.19–7.25 (m, 3H)

MS [EI, m/z]: 268 [M]$^+$

Anal. Calcd. for $C_{13}H_{17}ClN_2S$: C, 58.09; H, 6.38; N, 10.42. Found: C, 57.86; H, 6.29; N, 10.31.

EXAMPLE 6

1-(5-Chloro-2-methyl-phenyl)-3-isopropyl-3,4,5,6-tetrahydro-pyrimidine-2(1H)-thione Step A. N-isopropyl-1-amino-3-hydroxy-propane 1-Bromopropanol (20.85 g) was added dropwise to isopropylamine (35.4 g, 51 mL) over 30 minutes. The mixture was kept in an oil bath at 40–45° C. for 8 hours during which time a precipitate formed. After standing overnight at ambient temperature, the solid mass was treated with an ice cold aqueous sodium hydroxide solution (9 g in 21 mL of water) and then extracted with dichloromethane. The extracts were washed with brine, filtered and dried over anhydrous potassium carbonate. Removal of the solvent provided a volatile yellow oil (15.53 g, 88.5%) which was used as such in the next step.

NMR (DMSO-$d_6$, 400 MHz): δ0.89 (d, 6H), 1.49 (m, 2H), 2.52 (m, 2H), 2.63 (m, 1H), 3.4 (m, 2H).

Step B. 3-Bromo-N-isopropyl-1-amino-propane 1:1 salt with hydrobromic acid

An ice-cold solution of the amino alcohol of Step A (15.53 g) in carbon tetrachloride (150 mL) was saturated with HBr gas over ca. 30 minutes. The solvent was evaporated to yield an off-white spongy solid. Under ice cooling 48% HBr (150 mL) was added under nitrogen and the mixture was heated to reflux for 2.5 hours. The clear brown solution was evaporated in vacuo. The brown solid residue was twice azeotroped with water and toluene and the residue redissolved in ethanol. The solvent was evaporated and the residue was triturated with anhydrous ethyl ether-hexane to provide a solid which was collected, washed with hexane and dried. Trituration with anhydrous ether-hexane provided a grey solid (25.46 g, 73.5%), m.p. 175–176° C. (dec).

NMR (DMSO-$d_6$, 400 MHz): δ1.22 (d, 6H), 2.15 (m, 2H), 2.99 (m, 2H), 3.3 (m, 1H), 3.60 (m, 2H), 8.46 (broad, 2H).

Step C. N'-(5-Chloro-2-methyl-phenyl)-N-isopropyl-propane-1,3-diamine

A mixture of 4-chloro-2-methylaniline (16.12 g) and the hydrobromide salt of Step B (9.9 g) was heated at 70° C. until homogeneous and then at 100° C. for 30 minutes. The mixture was then cooled and partitioned between dichloromethane and 1N sodium hydroxide. The organic layer was washed with brine, dried over anhydrous potassium carbonate and evaporated to dryness. The residue was dissolved in dichloromethane and absorbed on a flash column of Merck-60 flash silica gel. Elution with a dichloromethane-methanol gradient (9:1 to 1:1) containing 0.2% ammonium hydroxide, provided the title compound (8.23 g, 90.4%) which was used as such in the next step.

NMR (DMSO-$d_6$, 400 MHz): δ0.97 (d, 6H), 1.69 (m, 2H), 2.02 (s, 3H), 2.60 (m, 2H), 2.66 (m, 1H), 3.09 (m, 2H), 5.61 (m, 1H), 6.45 (m, 2H), 6.91 (m, 1H).

Step D. 1-(5-Chloro-2-methyl-phenyl)-3-isopropyl-3,4,5,6-tetrahydro-pyrimidine-2(1H)-thione To a suspension of the diamine of Step C (6.47 g) in dioxane (100 mL) was added N,N'-thiocarbonyl-di-1,2,4-triazole (4.85 g) and the mixture was stirred at room temperature for 2 hours. Para-toluenesulfonic acid monohydrate (7.07 g) was added and the reaction mixture was heated at reflux under nitrogen until the reaction was complete by TLC (31 hours). Upon cooling the mixture was evaporated to dryness. The solid residue was redissolved in ethyl acetate, the solution was washed with water and brine, dried over magnesium sulfate and evaporated to dryness. The residue was dissolved in dichloromethane and absorbed onto a column of Merck-60 flash silica gel packed in hexane. Elution with a gradient of 20–25% ethyl acetate in hexane provided the title compound (5.81 g, 76.4%) as a white solid which was further triturated in hexane, m.p. 176–178° C.

NMR (DMSO-$d_6$, 400 MHz): δ1.10 (m, 6H), 2.01 (m, 2H), 2.10 (s, 3H), 3.3 and 3.52 (m, 4H), 5.62 (m, 1H), 7.20 (m, 3H).

MS (EI, m/z): 282/284 [M]$^+$

Anal. Calcd. for $C_{14}H_{19}ClN_2S$: C, 59.45; H, 6.77; N, 9.90. Found C, 59.43; H, 6.83; N, 9.87.

EXAMPLE 7

1-(4-Chloro-2-methyl-phenyl)-3-isopropyl-3,4,5,6-tetrahydro-pyrimidine-2(1H)-thione Step A. N'-(4-Chloro-2-methyl-phenyl)-N-isopropyl-propane-1,3-diamine A mixture of the hydrobromide salt of Example 6, Step B (9.9 g) and 4-chloro-2-methyl aniline (16.12 g) was heated at 70° C. under nitrogen until homogeneous and then at 100° C. for 20 minutes. After cooling, the brown solution was partitioned between ice-cold 1N sodium hydroxide and dichloromethane. The extracts were washed with brine, dried over anhydrous potassium carbonate and evaporated to dryness. The residue was dissolved in dichloromethane and absorbed on a column of Merck-60 flash silica gel. Elution with a dichloromethane-methanol gradient (from 9:1 to 1:1) containing 0.2% ammonium hydroxide, provided the title compound (8.2 g, 90.3%), as a brown solid, which was used as such in the next step.

NMR (DMSO-$d_6$, 400 MHz): δ0.96 (d, 6H), 1.68 (m, 2H), 2.04 (s, 3H), 2.59 (m, 2H), 2.66 (m, 1H), 3.08 (m, 2H), 5.42 (m, 1H), 6.45 (m, 1H), 6.99 (m, 2H)

MS (+FAB, m/z): 241/243 [M+H]$^+$.

Step B. 1-(4-Chloro-2-methyl-phenyl)-3-isopropyl-3,4,5,6-tetrahydro-pyrimidine-2(1H)-thione To a solution of the diamine of Step A (6 g) in dioxane (100 mL) under nitrogen was added N,N'-thiocarbonyl-di-1,2,4-triazole (4.5 g). After stirring at room temperature for 3 hours, para-toluene sulfonic acid monohydrate was added in one portion (9.5 g) and the mixture was heated at reflux for 8 hours. Additional para-toluene sulfonic acid monohydrate was added (1 g) and reflux was resumed for another 2 hours. The mixture was cooled and diluted with ethyl acetate. The precipitate was collected and washed with ethyl acetate. The combined filtrates were washed with brine, dried over magnesium sulfate, and evaporated to dryness. The residue was dissolved in dichloromethane and absorbed onto a column of Merck-60 flash silica gel. Elution with 20% ethyl acetate in hexane provided the title compound as a white crystalline solid (5.26 g, 74.6%). The material was slurried in hexane-ether, sonicated and collected to provide 4.91 g of pure product, m.p. 147–149° C.

NMR (DMSO-$d_6$, 400 MHz): δ1.10 (m, 6H), 2.01 (m, 2H), 2.12 (s, 3H), 3.31 and 3.48 (m, 4H), 5.62 (m, 1H), 7.10 (m, 1H), 7.20 (m, 1H), 7.29 (m, 1H)

MS (+FAB, m/z): 283/285 [M+H]$^+$

Anal. Calcd.for $C_{14}H_{19}ClN_2S$: C, 59.45; H, 6.77; N, 9.90. Found: C, 59.76; H, 6.87; N, 9.90.

EXAMPLE 8

3-Allyl-1-(5-chloro-2-methyl-phenyl)-3,4,5,6-tetrahydro-pyrimidine-2(1H)-thione

Step A. 1-(5-Chloro-2-methyl-phenyl)amino-3-hydroxy-propane

A mixture of 5-chloro-2-methylaniline (10.1 g) and 3-bromo-1-propanol (2.5 mL) were heated at 100° C. under nitrogen for 45 minutes. After cooling, a solid mass formed which was partitioned between dichloromethane and 1N sodium hydroxide. The organic phase was washed with brine, dried over anhydrous potassium carbonate, and concentrated in vacuo to give a brown oil. The crude material was dissolved in dichloromethane and absorbed onto a column of Merck-60 flash silica gel. Elution with 20% ethyl acetate in hexane gave the title compound (5.6 g, 98.1%) as a brown oil, which was used as such in the next step.

$^1$H NMR (DMSO-$d_6$, 400 MHz): δ1.68–1.75 (m, 2H), 2.01 (s, 3H), 3.08–3.13 (m, 2H), 3.48–3.53 (m, 2H), 4.56 (t, 1H), 5.13 (t, 1H), 6.45–6.48 (m, 2H), 6.91–6.93 (m, 1H)

MS [EI, m/z]: 199 [M]$^+$.

Step B. 3-Bromo-1-(5-chloro-2-methyl-phenyl) amino-propane 1:1 salt with hydrobromic acid A mixture of the amino alcohol of Step A (5.6 g) and 48% aqueous hydrobromic acid (56 mL) was heated at reflux under nitrogen for 1 hour. The hydrobromic acid was removed in vacuo and the solid residue azeotroped repeatedly with water and ethanol to provide the title compound (7.5 g, 77.7%) as a pale-orange solid, m.p. 154–156° C.

$^1$H NMR (DMSO-$d_6$, 400 MHz): δ2.06 (s, 3H), 2.08–2.13 (m, 2H), 3.20 (t, 2H), 3.61 (t, 2H), 6.10–6.40 (m, 2H), 6.56–6.59 (m, 2H), 6.96–6.98 (m, 1H)

MS [EI, m/z]: 261 [M]$^+$

Anal. Calcd. for $C_{10}H_{13}BrClN \cdot HBr$: C, 34.97; H, 4.11; N, 4.08. Found: C, 35.20; H, 4.05; N, 4.07.

Step C. N-Allyl-N'-(5-chloro-2-methyl-phenyl)-propane-1,3-diamine

A mixture of allylamine (1.0 mL) and the hydrobromide salt of Step B (1.0 g) was heated at 100° C. under nitrogen for 45 minutes. The reaction was cooled and partitioned between dichloromethane and 1 N sodium hydroxide. The aqueous layer was extracted with dichloromethane, the extracts were dried over sodium sulfate and concentrated in vacuo to give a yellow oil. The crude material was dissolved in dichloromethane and absorbed onto a column of Merck-60 flash silica gel. Elution with a solvent gradient (from 98:2 dichloromethane-methanol to 90:10 dichloromethane-methanol containing 0.2% ammonium hydroxide) provided the title compound (0.35 g, 50.5%) as a yellow oil which was used as such in the next step.

$^1$H NMR (DMSO-$d_6$, 400 MHz): δ1.68–1.74 (m, 2H), 2.01 (s, 3H), 2.61 (t, 2H), 3.06–3.25 (m, 5H), 5.03–5.06 (m, 1H), 5.13–5.19 (m, 1H), 5.47–5.50 (m, 1H, NH), 5.79–5.87 (m, 1H), 6.45–6.47 (m, 2H), 6.91–6.93 (m, 1H)

MS [+FAB, m/z]: 239 [M+H]$^+$.

Step D. 3-Allyl-1-(5-chloro-2-methyl-phenyl)-3,4,5,6-tetrahydro-pyrimidine-2(1H)-thione To an ice-cold solution of the diamine of Step C (3.4 g) and triethylamine (4.0 mL) in dry chloroform (50 mL) was added dropwise under nitrogen thiophosgene (1.1 mL). After 30 minutes at ambient temperature, additional triethylamine (1.0 mL) and thiophosgene (0.28 mL) were added. After 15 minutes, no starting material remained. The reaction was quenched with water, the pH adjusted to 8 with triethylamine, and extracted with dichloromethane. The extracts were combined, dried over sodium sulfate and concentrated in vacuo to give a brown oil. The crude material was dissolved in dichloromethane and absorbed onto a column of Merck-60 flash silica gel. Elution with 10% ethyl acetate in hexane provided a yellow solid which was triturated with diethyl ether to give the title compound (1.69 g, 42.4%) as a white solid, m.p. 71–72° C.

$^1$H NMR (DMSO-$d_6$, 400 MHz): δ2.02–2.12 (m, 2H), 2.13 (s, 3H), 3.36–3.61 (m, 4H), 4.45–4.62 (m, 2H), 5.16–5.20 (m, 2H), 5.78–5.87 (m, 1H), 7.20–7.26 (m, 3H)

MS [EI, m/z]: 280 [M]$^+$

Anal. Calcd. for $C_{14}H_{17}ClN_2S$: C, 59.88; H, 6.10; N, 9.98. Found: C, 59.91; H, 6.14; N, 9.83.

EXAMPLE 9

1-(5-Chloro-2-methyl-phenyl)-3-methyl-3,4,5,6-tetrahydro-pyrimidine-2(1H)-thione

Step A. N'-(5-Chloro-2-methyl-phenyl)-N-methyl-propane-1,3-diamine

To an 8.03 M solution of methylamine in ethanol (27 mL) was added the hydrobromide salt of Example 8, Step B (7.5 g). The reaction was stirred at ambient temperature for 18 hours. The solvent was removed in vacuo and the residue partitioned between dichloromethane and 1N sodium hydroxide. The organic phase was washed with brine, dried over sodium sulfate and concentrated in vacuo to give a brown oil. The crude material was dissolved in dichloromethane and absorbed onto a column of Merck-60 flash silica gel. Elution with a solvent gradient (from 98:2 to 90:10 dichloromethane-methanol containing 0.2% ammonium hydroxide) gave the title compound (3.9 g, 84.1%) as a pale orange oil, which was used as such in the next step.

$^1$H NMR (DMSO-d$_6$, 400 MHz): δ1.67–1.71 (m, 2H), 2.01 (s, 3H), 2.28 (s, 3H), 2.56 (t, 2H), 2.96–3.04 (m, 1H), 3.05–3.09 (m, 2H), 5.48–5.56 (m, 1H), 6.44–6.47 (m, 2H), 6.90–6.92 (m, 1H)

MS [EI, m/z]: 212 [M]$^+$.

Step B. 1-(5-Chloro-2-methyl-phenyl)-3-methyl-3,4,5,6-tetrahydro-pyrimidine-2-(1H)-thione To a solution of the diamine of Step A (3.8 g) in dioxane (100 mL) under nitrogen was added 1,1'-thiocarbonyl-di-1,2,4-triazole (3.38 g). After 45 minutes additional thiocarbonyl reagent (0.5 g) was added, followed after 30 minutes by para-toluenesulfonic acid monohydrate (6.88 g). The reaction mixture was heated at reflux for 4 hours at which point additional para-toluenesulfonic acid monohydrate (2.0 g) was added. After refluxing for 18 hours, another portion of para-toluenesulfonic acid monohydrate (1.5 g) was added. The reaction mixture was refluxed for an additional 24 hours, cooled and concentrated in vacuo to give a brown oil which crystallized on standing. The crude material was dissolved in dichloromethane and absorbed onto a column of Merck-60 flash silica gel. Elution with 20% ethyl acetate in hexane provided a light pink solid which was triturated with diethyl ether to give the title compound (2.9 g, 63.9%) as a white solid, m.p. 143–145° C.

$^1$H NMR (DMSO-d$_6$, 400 MHz): δ2.04–2.12 (m, 2H), 2.13 (s, 3H), 3.31 (s, 3H), 3.34–3.60 (m, 4H), 7.19–7.25 (m, 3H)

MS [EI, m/z]: 254 [M]$^+$

Anal. Calcd. for $C_{12}H_{15}ClN_2S$: C, 56.57; H, 5.93; N, 11.00. Found: C, 56.23; H, 5.75; N, 10.86.

EXAMPLE 10

3-Allyl-1-(4-chloro-2-methyl-phenly)-3,4,5,6-tetrahydro-pyrimidine-2(1H)-thione

Step A. 1-(4-Chloro-2-methyl-phenyl)amino-3-hydroxy-propane

A mixture of 4-chloro-2-methylaniline (35.7 g) and 3-bromo-1-propanol (8.75 g) was heated at 100° C. under nitrogen for 1 hour. After cooling, a solid mass formed which was partitioned between dichloromethane and 1N sodium hydroxide. The organic layer was washed with brine, dried over anhydrous potassium carbonate and concentrated in vacuo to give a brown oil. The crude material was dissolved in dichloromethane and absorbed onto a column of Merck-60 flash silica gel. Elution with a solvent gradient (from 100% dichloromethane to 95:5 dichloromethane-methanol) provided the title product (18.0 g, 90%) as a brown oil, which was used as such in the next step.

NMR (DMSO-d$_6$, 400 MHz): δ1.68–1.74 (m, 2H), 2.04 (s, 3H), 3.08–3.13 (m, 2H), 3.48–3.53 (m, 2H), 4.55 (t, 1H), 4.96 (t, 1H), 6.46–6.49 (m, 1H), 6.97–7.01 (m, 2H)

MS [EI, m/z]: 199 [M]$^+$.

Step B. 1-(4-Chloro-2-methyl-phenyl)amino-3-bromo-propane 1:1 salt with hydrobromic acid A mixture of the amino alcohol of Step A (7.0 g) and 48% aqueous hydrobromic acid (70 mL) was heated at reflux under nitrogen for 2 hours. After cooling, the hydrobromic acid was removed in high vacuo. The solid residue was then washed with water and ethanol and dried in high vacuo to give the title compound (10.7 g, 89.0%) as a pale-orange solid, m.p. 145–148° C.

NMR (DMSO-d$_6$, 400 MHz): δ2.09–2.14 (m, 2H), 2.18 (s, 3H), 3.23 (t, 2H), 3.61 (t, 2H), 5.50–6.30 (m, 2H), 6.81–6.83 (m, 1H), 7.13–7.16 (m, 2H)

MS [EI, m/z]: 261 [M]$^+$

Anal. Calcd. for $C_{10}H_{13}BrClN·HBr$: C, 34.97; H, 4.11; N, 4.08. Found: C, 35.12; H, 4.02; N, 4.07.

Step C. N-Allyl-N'-(4-chloro-2-methyl-phenyl)-propane-1,3-diamine

A mixture of allylamine (18 mL) and the hydrobromide salt of Step B (8.2 g) was heated at 100° C. under nitrogen for 30 minutes. The reaction mixture was cooled and partitioned between dichloromethane and 1N sodium hydroxide. The aqueous layer was extracted with dichloromethane and the combined organic layers were dried over sodium sulfate and concentrated in vacuo to give a yellow oil. The crude material was dissolved in dichloromethane and absorbed onto a column of Merck-60 flash silica gel. Elution with a solvent gradient (from 98:2 dichloromethane-methanol to 95:5 dichloromethane-methanol containing 0.2% ammonium hydroxide) gave the title compound (5.3 g, 92.9%) as a light brown oil which was used as such in the next step.

NMR (DMSO-d$_6$, 400 MHz): δ1.67–1.73 (m, 2H), 2.04 (s, 3H), 2.59 (t, 2H), 3.05–3.16 (m, 5H), 5.01–5.04 (m, 1H), 5.11–5.16 (m, 1H), 5.26–5.36 (m, 1H), 5.78–5.87 (m, 1H), 6.45–6.47 (m, 1H), 6.98–7.00 (m, 2H)

MS [+FAB, m/z]: 239 [M+H]$^+$.

Step D. 3-Allyl-1-(4-chloro-2-methyl-phenyl)-3,4,5,6-tetrahydro-pyrimidine-2(1H)-thione To a solution of the diamine of Step C (5.6 g) and triethylamine (6.6 mL) in dry chloroform (70 mL) under nitrogen was added thiophosgene (1.79 mL). After 30 minutes at ambient temperature, additional thiophosgene (0.6 mL) was added. After 15 minutes, the reaction was quenched with water and extracted with dichloromethane. The organic layers were combined, dried over sodium sulfate and concentrated in vacuo to give a brown oil. The crude material was dissolved in dichloromethane and absorbed onto a column of Merck-60 flash silica gel. Elution with 11% ethyl acetate in hexane provided a yellow solid which was triturated with diethyl ether to give the title compound (3.1 g, 47.0%) as a white solid, m.p. 101–103° C.

NMR (DMSO-d$_6$, 400 MHz): δ2.02–2.12 (m, 2H), 2.15 (s, 3H), 3.36–3.58 (m, 4H), 4.44–4.63 (m, 2H), 5.16–5.23 (m, 2H), 5.78–5.87 (m, 1H), 7.12–7.31 (m, 3H)

MS [+FAB, m/z]: 281 [M+H]$^+$

Anal. Calcd. for $C_{14}H_{17}ClN_2S$: C, 59.88; H, 6.10; N, 9.98. Found: C, 59.68; H, 6.26; N, 9.94.

EXAMPLE 11

1-(4-Chloro-2-methyl-phenyl)-3-methyl-3,4,5,6-tetrahydro-pyrimidine-2(1H)thione

Step A. N'-(4-Chloro-2-methyl)phenyl)-N-methyl-propane-1,3-diamine

To an 8.03 M solution of methylamine in ethanol (38 mL) was added the 1-(4-chloro-2-methyl-phenyl)amino-3- bromo-propane hydrobromide salt of Example 10, Step B (10.6 g). The reaction mixture was stirred at ambient temperature for 30 minutes. The ethanol was removed in vacuo and the residue was partitioned between dichloromethane and 1N sodium hydroxide. The organic phase was washed with brine, dried over sodium sulfate and concentrated in vacuo to give a brown oil. The crude material was dissolved in dichloromethane and absorbed onto a column of Merck-60 flash silica gel. Elution with a solvent gradient (from 100% dichloromethane to 98:2 dichloromethane-methanol containing 0.2% ammonium hydroxide) gave the title compound (4.1 g, 62.6%) as a pale orange oil, which was used as such in the next step.

NMR (DMSO-$d_6$, 400 MHz): $\delta$1.66–1.72 (m, 2H), 2.04 (s, 3H), 2.28 (s, 3H), 2.56 (t, 2H), 3.04–3.30 (m, 3H), 5.28–5.38 (m, 1H), 6.45–6.47 (m, 1H), 6.97–7.01 (m, 2H)

MS [+FAB, m/z]: 213 [M+H]$^+$.

Step B. 1-(4-Chloro-2-methyl-phenyl)-3-methyl-3,4,5,6-tetrahydro-pyrimidin-2(1H)-thione To a solution of the diamine of Step A (4.0 g) in dioxane (100 mL) under nitrogen was added 1,1'-thiocarbonyl-di-1,2,4-triazole (3.5 g). After 30 minutes additional thiocarbonyl reagent (1.0 g) was added. After 30 minutes para-toluenesulfonic acid monohydrate (10.2 g) was added in one portion and the reaction mixture was heated at reflux for 24 hours. Additional para-toluenesulfonic acid monohydrate (2.5 g) was added at this point and after another 24 hours at reflux, the reaction was cooled and filtered. The filtrate was concentrated in vacuo to give a brown oil. The crude material was dissolved in dichloromethane and absorbed onto a column of Merck-60 flash silica gel. Elution with 20% ethyl acetate in hexane gave the title product (2.7 g, 56.4%) as a white solid, m.p. 143–145° C.

NMR (DMSO-$d_6$, 400 MHz): $\delta$2.04–2.11 (m, 2H), 2.14 (s, 3H), 3.31 (s, 3H), 3.34–3.57 (m, 4H), 7.10–7.30 (m, 3H)

MS [EI, m/z]: 254 [M]$^+$

Anal. Calcd. for $C_{12}H_{15}ClN_2S$: C, 56.57; H, 5.93; N, 11.00. Found: C, 56.37; H, 5.97; N, 11.01.

EXAMPLE 12

3-Allyl-1-(6-chloro-2-methyl-phenyl)-3,4,5,6-tetrahydro-pyrimidine-2(1H)-thione

Step A. 1-(6-Chloro-2-methyl-phenyl)amino-3-hydroxy-propane

A mixture of the 6-chloro-2-methyl aniline (70.8 g) and 3-bromo-1-propanol (27.8 g) was heated under nitrogen to 100° C. for 2 hours. The mixture was cooled and partitioned between dichloromethane and 1N sodium hydroxide. The organic layer was washed with 20% aqueous sodium chloride, dried over anhydrous potassium carbonate and evaporated to dryness. The residue was flash chromatographed on Merck-60 flash silica gel. Elution with a hexane-ethyl acetate gradient (from 8:1 to 3:1) provided the title compound (30.86 g, 77.5%) as a pale yellow oil, which was used as such in the next step.

Step B. 1-(6-Chloro-2-methyl-phenyl)amino-3-bromo-propane 1:1 salt with hydrobromic acid A mixture of the amino alcohol of Step A (13.0 g) and 48% aqueous HBr (130 mL) were heated at reflux under nitrogen for 2.5 hours. After cooling, the hydrobromic acid was removed in vacuo. The solid residue was then washed with water and ethanol and dried in vacuo to give the title compound (21.1 g, 94.5%) as an orange to brown solid, m.p. 161–163° C.

NMR (DMSO-$d_6$, 400 MHz): $\delta$2.10 (m, 2H), 2.35 (s, 3H), 3.26 (m, 2H), 3.61 (m, 2H), 7.03 (m, 1H), 7.18 (m, 1H), 7.30 (m, 1H)

MS [EI, m/z]: 261 [M]$^+$

Anal. Calcd. for $C_{10}H_{13}BrClN \cdot HBr$: C, 34.97; H, 4.11; N, 4.08. Found: C, 35.27; H, 4.00; N, 4.12.

Step C. N-Allyl-N'-(6-chloro-2-methyl-phenyl)-propane-1,3-diamine

A mixture of allylamine (20 mL) and the hydrobromide salt of Step B (8.6 g) was heated at 100° C. under nitrogen for 30 minutes. The reaction mixture was cooled and partitioned between dichoromethane and 1N sodium hydroxide. The aqueous layer was extracted with dichloromethane, and the combined organic layers were dried over sodium sulfate and concentrated in vacuo to give a yellow oil. The crude material was dissolved in dichloromethane and absorbed onto a column of Merck-60 flash silica gel. Elution with 1:1 ethyl acetate-hexane followed by 80:20 dichloromethane-methanol containing 0.2% ammonium hydroxide gave the title compound (5.0 g, 83.8%) as a yellow oil which was used as such in the next step.

NMR (DMSO-$d_6$, 400 MHz): $\delta$1.56–1.63 (m, 2H), 2.24 (s, 3H), 2.54 (t, 2H), 3.05–3.20 (m, 5H), 4.25–4.45 (m, 1H), 4.99–5.15 (m, 2H), 5.76–5.86 (m, 1H), 6.73–6.77 (m, 1H), 7.01–7.04 (m, 1H), 7.13–7.16 (m, 1H)

MS [EI, m/z]: 238 [M]$^+$.

Step D. 3-Allyl-1-(6-chloro-2-methyl-phenyl)-3,4,5,6-tetrahydro-pyrimidine-2(1H)-thione To an ice-cold solution of the diamine of Step C (4.9 g) and triethylamine (5.8 mL) in chloroform (70 mL) under nitrogen was added thiophosgene (1.6 mL). After 20 minutes at ambient temperature, additional thiophosgene (0.5 mL) was added. After 15 minutes, the reaction was quenched with water and extracted with dichloromethane. The extracts were dried over sodium sulfate and concentrated in vacuo to give a brown oil. The crude material was dissolved in dichloromethane and absorbed onto a column of Merck-60 flash silica gel. Elution with 11% ethyl acetate in hexane provided a yellow solid which was triturated with diethyl ether to give the title product (3.2 g, 55.6%) as a white solid, m.p. 82–84° C.

NMR (DMSO-$d_6$, 400 MHz): $\delta$2.09–2.12 (m, 2H), 2.21 (s, 3H), 3.42–3.46 (m, 4H), 4.52–4.57 (m, 2H), 5.17–5.23 (m, 2H), 5.79–5.86 (m, 1H), 7.15–7.21 (m, 2H), 7.30–7.32 (m, 1H)

MS [EI, m/z]: 280 [M]$^+$

Anal. Calcd. for $C_{14}H_{17}ClN_2S$: C, 59.88; H, 6.10; N, 9.97. Found: C, 59.75; H, 5.99; N, 9.80.

EXAMPLE 13

1-(6-Chloro-2-methyl-phenyl)-3-methyl-3,4,5,6-tetrahydro-pyrimidine-2(1H)-thione Step A. N'-(6-Chloro-2-methyl-phenyl)-N-methyl-propane-1,3-diamine To an 8.03 M solution of methylamine in ethanol (31 mL) was added the hydrobromide salt of Example 12, Step B (8.6 g) and the mixture was stirred at ambient temperature for 17 hours. The ethanol was removed in vacuo and the residue was partitioned between dichloromethane and 1N sodium hydroxide. The organic phase was washed with brine, dried over sodium sulfate, and concentrated in vacuo to give a yellow oil. The crude material was dissolved in dichloromethane and absorbed onto a column of Merck-60 flash silica gel. Elution with a solvent gradient (from 98:2 to 80:20 dichloromethane-methanol containing 0.2% ammonium hydroxide) gave the title compound (3.9 g, 84.1%) as a pale yellow oil, which was used as such in the next step.

NMR (DMSO-$d_6$, 400MHz): δ1.55–1.62 (m, 2H), 2.23 (s, 3H), 2.24 (s, 3H), 2.51 (t, 2H), 2.95–3.12 (m, 3H, NH), 4.25–4.50 (m, 1H), 6.72–6.76 (m, 1H), 7.01–7.03 (m, 1H), 7.13–7.15 (m, 1H)

MS [+FAB, m/z]: 213 [M+H]$^+$.

Step B. 1-(6-Chloro-2-methyl-phenyl)-3-methyl-3,4, 5,6-tetrahydro-pyrimidine-2(1H)-thione To a solution of the diamine of Step A (4.16 g) in dioxane (110 mL) was added under nitrogen 1,1'-thiocarbonyl-di-1, 2,4-triazole (7.12 g). After 30 minutes, para-toluenesulfonic acid monohydrate (15.1 g) was added and the reaction mixture was heated at reflux for 20 hours. More para-toluenesulfonic acid monohydrate (4.0 g) was added at this point, and after an additional 2.5 hours at reflux, the reaction was cooled and filtered. The filtrate was concentrated in vacuo to give an orange oil. The crude material was dissolved in dichloromethane and absorbed onto a column of Merck-60 flash silica gel. Elution with 20% ethyl acetate in hexane provided a white solid which was triturated with diethyl ether to give the title product (2.0 g, 40.3%) as a white solid, m.p. 164–165° C.

NMR (DMSO-$d_6$, 400 MHz): δ2.09–2.13 (m, 2H), 2.20 (s, 3H), 3.32 (s, 3H), 3.41 (t, 2H), 3.52 (t, 2H), 7.14–7.21 (m, 2H), 7.29–7.31 (m, 1H)

MS [EI, m/z]: 254 [M]$^+$

Anal. Calcd. for $C_{12}H_{15}ClN_2S$: C, 56.57; H, 5.93; N, 10.99. Found: C, 56.19; H, 5.71; N, 10.67.

EXAMPLE 14

1-(5-Chloro-2-methyl-phenyl)-3-isobutyl-3,4,5,6-tetrahydro-pyrimidine-2-(1H)-thione Step A. N'-(5-Chloro-2-methyl-phenyl)-N-isobutyl-propane-1,3-diamine A mixture of isobutylamine (27.2 mL) and the hydrobromide salt of Example 8, Step B (9.4 g) was heated at 90° C. under nitrogen for 1 hour. The reaction was cooled and partitioned between dichloromethane and 1N sodium hydroxide. The aqueous layer was extracted with dichloromethane, and the combined extracts were dried over sodium sulfate and concentrated in vacuo to give a brown oil. The crude material was dissolved in dichloromethane and absorbed onto a column of Merck-60 flash silica gel. Elution with 25% ethyl acetate in hexane followed by 80:20 dichloromethane-methanol containing 0.2% ammonium hydroxide gave the title compound (6.0 g, 85.9%) as a brown oil, which was used as such in the next step.

NMR(DMSO-$d_6$, 400MHz): δ0.86 (d, 6H), 1.63–1.74 (m, 3H), 2.02 (s, 3H), 2.31 (d, 2H), 2.59 (t, 2H), 3.08–3.12 (m, 2H), 5.43–5.46 (m, 1H), 6.45–6.47 (m, 2H), 6.90–6.93 (m, 1H)

MS [EI, m/z]: 254 [M]$^+$.

Step B. 1-(5-Chloro-2-methyl-phenyl)-3-isobutyl-3, 4,5,6-tetrahydro-pyrimidine-2-(1H)-thione To an ice-cold solution of the diamine of Step A (5.0 g) and triethylamine (5.2 mL) in dry chloroform (50 mL) under nitrogen was added thiophosgene (1.5 mL). After 5 minutes at ambient temperature, additional thiophosgene (1.0 mL) was added. After 10 minutes the reaction was quenched with water and extracted with dichloromethane. The combined extracts were dried over sodium sulfate and concentrated in vacuo to give a brown oil. The crude material was dissolved in dichloromethane and absorbed onto a column of Merck-60 flash silica gel. Elution with 11% ethyl acetate in hexane provided a pale brown solid which was triturated with diethyl ether to give the title product (2.8 g, 48.1%) as a white solid, m.p. 96–98° C.

NMR (DMSO-$d_6$, 400 MHz): δ0.89 (d, 6H), 2.04–2.11 (m, 2H), 2.12 (s, 3H), 2.14–2.20 (m, 1H), 3.35–3.92 (m, 6H), 7.19–7.25 (m, 3H)

MS [EI, m/z]: 296 [M]$^+$

Anal. Calcd. for $C_{15}H_{21}ClN_2S$: C, 60.69; H, 7.13; N, 9.44. Found: C, 60.97; H, 7.34; N, 9.49.

EXAMPLE 15

1-(6-Chloro-2-methyl-phenyl)-3-isopropyl-3,4,5,6-tetrahydro-pyrimidine-2(1H)-thione Step A. N'-(6-Chloro-2-methyl-phenyl)-N-isopropyl-propane-1,3-diamine A mixture of isopropylamine (18.3 mL) and the hydrobromide salt of Example 7, Step B (15 g) was heated at 100° C. under nitrogen for 45 minutes. The reaction was cooled and partitioned between water and ethyl acetate. The aqueous layer was extracted with ethyl acetate, and the combined extracts were dried over sodium sulfate and concentrated in vacuo. The crude material was dissolved in dichloromethane and absorbed onto a column of Merck-60 flash silica gel. Elution with a solvent gradient (from 95:5 to 80:20 dichloromethane-methanol containing 0.2% ammonium hydroxide) gave the title compound (48.25 g, 78.4%) as a yellow oil which was used as such in the next step.

NMR (DMSO-$d_6$, 400 MHz): δ0.94 (d, 6H), 1.55–1.62 (m, 2H), 2.24 (s, 3H), 2.55 (t, 2H), 2.63–2.69 (m, 1H), 3.08–3.14 (m, 2H), 4.35–4.52 (m, 1H), 6.73–6.77 (m, 1H), 7.01–7.03 (m,1H), 7.13–7.15 (m, 1H)

MS [EI, m/z]: 240 [M]$^+$.

Step B. 1-(6-Chloro-2-methyl-phenyl)-3-isopropyl-3,4,5,6-tetrahydro-pyrimidine-2(1H)-thione To an ice-cold solution of the diamine of Step A (8.2 g) and triethylamine (9.09 mL) in dry chloroform (180 mL) under nitrogen was added thiophosgene (3.92 mL). After 10 minutes in the cold and 30 minutes at ambient temperature, the pH was adjusted to 8 with triethylamine and the reaction was quenched with water and extracted with dichloromethane. The combined extracts were dried over sodium sulfate, and concentrated in vacuo to give a brown oil. The crude material was dissolved in dichloromethane and absorbed onto a column of Merck-60 flash silica gel. Elution with 11% ethyl acetate in hexane provided a white crystalline solid which was triturated with diethyl ether to give the title product (4.5 g, 46%), m.p. 135–136° C.

NMR (DMSO-$d_6$, 400MHz): δ1.11 (d, 6H), 2.03–2.06 (m, 2H), 2.18 (s, 3H), 3.34–3.38 (m, 4H), 5.60–5.63 (m, 1H), 7.15–7.18 (m, 2H), 7.29–7.31 (m, 1H)

MS [+FAB, m/z]: 283 [M+H]$^+$.

Anal. Calcd. for $C_{14}H_{19}ClN_2S$: C, 59.45; H, 6.77; N, 9.91. Found: C, 59.65; H, 6.82; N, 9.89.

EXAMPLE 16

1-(6-Chloro-2-methyl-phenyl)-3-ethyl-3,4,5,6-tetrahydro-pyrimidine-2(1H)-thione

Step A. N'-(6-Chloro-2-methyl-phenyl)-N-ethyl-propane-1,3-diamine

A mixture of a 2.0 M solution of ethylamine in tetrahydrofuran (139.5 mL) and the hydrobromide salt of Example 12, Step A (9.5 g) was stirred at ambient temperature under nitrogen for 48 hours. The tetrahydrofuran was removed in vacuo and the residue was partitioned between dichloromethane and 1N sodium hydroxide. The extracts were washed with brine, dried over sodium sulfate, and concentrated in vacuo to give a brown oil. The crude material was dissolved in dichloromethane and absorbed onto a column of Merck-60 flash silica gel. Elution with a solvent gradient (from 95:5 to 80:20 dichloromethane-methanol containing 0.2% ammonium hydroxide) gave the title compound (3.4 g, 54.3%) as a yellow oil, which was used as such in the next step.

NMR (DMSO-$d_6$, 400 MHz): δ0.98 (t, 3H), 1.56–1.62 (m, 2H), 2.24 (s, 3H), 2.49 (q, 2H), 2.56 (t, 2H), 2.80–3.05 (m, 1H), 3.13 (t, 2H), 4.35–4.50 (m, 1H), 6.73–6.77 (m, 1H), 7.01–7.04 (m, 1H), 7.13–7.15 (m, 1H)

MS [EI, m/z]: 226 [M]$^+$.

Step B. 1-(6-Chloro-2-methyl-phenyl)-3-ethyl-3,4,5,6-tetrahydro-pyrimidine-2(1H)-thione To an ice-cold solution of the diamine of Step A (3.4 g) and triethylamine (4.0 mL) in dry chloroform (50 mL) was added thiophosgene (1.7 mL). After 20 minutes at ambient temperature, the reaction was quenched with water and extracted with dichloromethane. The extracts were combined, dried over sodium sulfate and concentrated in vacuo to give a brown oil. The crude material was dissolved in dichloromethane and absorbed onto a column of Merck-60 flash silica gel. Elution with 11% ethyl acetate in hexane provided an orange solid which was triturated with diethyl ether to give the title product (2.4 g, 59.5%) as a white solid, m.p. 88–90° C.

NMR (DMSO-$d_6$, 400 MHz): δ1.13 (t, 3H), 2.07–2.11 (m, 2H), 2.19 (s, 3H), 3.37–3.41 (m, 2H), 3.48–3.50 (m, 2H), 3.81–3.94 (m, 2H), 7.14–7.20 (m, 2H), 7.29–7.31 (m, 1H).

MS [+FAB, m/z]: 269 [M+H]$^+$

Anal. Calcd. for $C_{13}H_{17}ClN_2S$: C, 58.09; H, 6.37; N, 10.42. Found: C, 57.94; H, 6.43; N, 10.27.

EXAMPLE 17

1-(4-Chloro-2-methyl-phenyl)-3-isobutyl-3,4,5,6-tetrahydro-pyrimidine-2(1H)-thione Step A. N'-(4-Chloro-2-methyl-phenyl)-N-isobutyl-propane-1,3-diamine A mixture of isobutylamine (27 mL) and the hydrobromide salt of Example 10, Step B (9.3 g) was heated under nitrogen at 90° C. for 2 hours. The reaction was cooled and partitioned between dichloromethane and 1N sodium hydroxide. The aqueous layer was extracted with dichloromethane and the combined extracts were dried over sodium sulfate and concentrated in vacuo to give a brown oil. The crude material was dissolved in dichloromethane and absorbed onto a column of Merck-60 flash silica gel. Elution with 33% ethyl acetate in hexane followed by 80:20 dichloromethane-methanol containing 0.2% ammonium hydroxide gave the title compound (4.9 g, 71.0%) as a brown oil, which was used a such in the next step.

NMR (DMSO-$d_6$, 400 MHz): δ0.85 (d, 6H), 1.62–1.73 (m, 3H), 2.04 (s, 3H), 2.31 (d, 2H), 2.59 (t, 2H), 3.06–3.11 (m, 2H), 5.20–5.30 (m, 1H), 6.46–6.48 (m, 1H), 6.98–7.00 (m, 2H)

MS [EI, m/z]: 254 [M]$^+$.

Step B. 1-(4-Chloro-2-methyl-phenyl)-3-isobutyl-3,4,5,6-tetrahydro-pyrimidine-2(1H)-thione To an ice-cold solution of the diamine of Step A (4.8 g) and triethylamine (5.0 mL) in dry chloroform (75 mL) was added thiophosgene (2.2 mL). After 10 minutes at ambient temperature, the reaction was quenched with water and extracted with dichloromethane. The extracts were combined, dried over sodium sulfate and concentrated in vacuo to give a brown oil. The crude material was dissolved in dichloromethane and absorbed onto a column of Merck-60 flash silica gel. Elution with 11% ethyl acetate in hexane provided a yellow solid which was triturated with diethyl ether to give the title product (2.4 g, 43.0%) as a white solid, m.p. 88–90° C.

NMR (DMSO-$d_6$, 400 MHz): δ0.88 (d, 6H), 2.04–2.10 (m, 2H), 2.14 (s, 3H), 2.16–2.21 (m, 1H), 3.35–3.91 (m, 6H), 7.09–7.29 (m, 3H).

MS [EI, m/z]: 296 [M]$^+$

Anal. Calcd. for $C_{15}H_{21}ClN_2S$: C, 60.69; H, 7.13; N, 9.44. Found: C, 60.48; H, 6.95; N, 9.33.

EXAMPLE 18

1-(6-Chloro-2-methyl-phenyl)-3-cyclobutyl-3,4,5,6-tetrahydro-pyrimidine-2(1H)-thione Step A. N'-(6-Chloro-2-methyl-phenyl)-N-cyclobutyl-propane-1,3-diamine A mixture of the hydrobromide salt of Example 12, Step B (6.64 g) and cyclobutylamine (4.15 g) was heated at 90° C. for 1.5 hours. The cooled mixture was diluted with water and extracted with dichloromethane. The extracts were washed with 20% aqueous sodium chloride, dried over anhydrous potassium carbonate and evaporated to a brown oil, which was flash chromatographed on Merck-60 flash silica gel (eluant: hexane-EtOAc 1:1 to remove less polar impurities, followed by dichloromethane-methanol-ammonium hydroxide 95:5:0.1) to provide the title compound (3.08 g, 63.5%), which was used as such in the next step.

Step B. 1-(6-Chloro-2-methyl-phenyl)-3-cyclobutyl-3,4,5,6-tetrahydropyrimidine-2(1H)-thione To a solution of the diamine of Step A (3.28 g) in dry chloroform (48 mL) was added dropwise under nitrogen at 0° C. triethylamine (3.62 mL). Thiophosgene (1.49 mL) was then added dropwise via syringe and the mixture was stirred in the cold for another 15 minutes. Stirring was continued at room temperature for 1.5 hours, water was added and the the pH was adjusted to 8 with triethylamine. The aqueous layer was further extracted with dichloromethane and the combined extracts were washed with 20% aqueous sodium chloride, dried over anhydrous potasium carbonate and evaporated to dryness. The residue was dissolved in dichloromethane and absorbed onto a column of Merck-60 flash silica gel. Elution with hexane-ethyl acetate 9:1 provided the title compound (3.1 g, 81%) which was further triturated and sonicated with hexane and hexane-ether. The off-white solid was collected, washed with hexane and dried (2.69 g, 75.3%), m.p. 89–91° C.

NMR (DMSO-$d_6$, 400 MHz): δ1.60 (m, 2H), 2.08 (m, 6H), 2.16 (s, 3H), 3.36 (t, 2H), 3.51 (t, 2H), 5.74 (m, 1H), 7.16 (m, 2H), 7.30 (m, 1H)

MS (EI, m/z): 294/296 [M]$^+$.

Anal. Calcd. for $C_{15}H_{19}ClN_2S$: C, 61.10; H, 6.50; N, 9.50. Found: C, 61.39; H, 6.51; N, 9.49.

EXAMPLE 19

1-(5-Chloro-2-methyl-phenyl)-3-cyclobutyl-3,4,5,6-tetrahydro-pyrimidine-2(1H)-thione Step A. N'-(5-Chloro-2-methyl-phenyl)-N-cyclobutyl-propane-1,3-diamine To neat cyclobutylamine (10.0 mL) was added the hydrobromide salt of Example 8, Step B in two equal portions (2×4.3 g) 15 minutes apart at ambient temperature. The mixture was heated at reflux under nitrogen for 30 minutes, then cooled and partitioned between dichloromethane and 1N sodium hydroxide The aqueous layer was extracted with dichloromethane, the combined extracts were dried over sodium sulfate and concentrated in vacuo to give a brown oil. The crude material was dissolved in dichloromethane and absorbed onto a column of Merck-60 flash silica gel. Elution with a solvent gradient (from 98:2 dichloromethane-methanol to 80:20 dichloromethane-methanol containing 0.2% ammonium hydroxide) gave the title compound (3.7 g, 58.5%) as a brown solid, which was used as such in the next step.

NMR (DMSO-$d_6$, 400 MHz): δ1.51–1.69 (m, 6H), 2.01 (s, 3H), 2.05–2.11 (m, 2H), 2.52 (t, 2H), 3.06–3.30 (m, 4H), 5.58–5.61 (m, 1H), 6.44–6.47 (m, 2H), 6.90–6.92 (m, 1H)

MS [EI, m/z]: 252 [M]$^+$.

Step B. 1-(5-Chloro-2-methyl-phenyl)-3-cyclobutyl-3,4,5,6-tetrahydro-pyrimidine-2(1H)-thione To an ice-cold solution of the diamine of Step A (3.6 g) and triethylamine (3.8 mL) in dry chloroform (40 mL) under nitrogen was added thiophosgene (1.7 mL). After 10 minutes at ambient temperature, the reaction was quenched with water and extracted with dichloromethane. The extracts were combined and dried over sodium sulfate and concentrated in vacuo to give a brown solid. The crude material was dissolved in dichloromethane and absorbed onto a column of Merck-60 flash silica gel. Elution with a solvent gradient (from 11% ethyl acetate in hexane to 8:1:1 hexane-ethyl acetate-dichloromethane) provided pure material which was triturated with diethyl ether to give the title product (2.3 g, 54.9%) as a white solid, m.p. 152–154° C.

NMR (DMSO-$d_6$, 400 MHz): δ1.54–1.65 (m, 2H), 2.00–2.21 (m, 9H), 3.28–3.55 (m, 4H), 5.75–5.80 (m, 1H), 7.19–7.25 (m, 3H)

MS [EI, m/z]: 294 [M]$^+$

Anal. Calcd. for $C_{15}H_{19}ClN_2S$: C, 61.10; H, 6.50; N, 9.50. Found: C, 60.77; H, 6.52; N, 9.43.

EXAMPLE 20

1-(6-Chloro-2-methyl-phenyl)-3-isobutyl-3,4,5,6-tetrahydro-pyrimidine-2(1H)-thione Step A. N'-(6-Chloro-2-methyl-phenyl)-N-isobutyl-propane-1,3-diamine Under cooling the hydrobromide salt of Example 12, Step B (6.82 g) was mixed with isobutylamine (5.85 g). The mixture was warmed to 85° C. under nitrogen until homogeneous and then refluxed for 2.5 hours. After cooling, it was diluted with water and the basic solution extracted with dichloromethane. The extracts were washed with 20% aqueous sodium chloride, dried over anhydrous potassium carbonate and evaporated to a brown oil which was flash chromatographed (on Merck-60 flash silica gel). The less polar impurities were eluted with 1:1 hexane- EtOAc and the desired material with 95:5:0.1 dichloromethane-methanol-ammonium hydroxide. The low melting material (3.82 g, 75%) was used as such in the next step.

NMR (DMSO-$d_6$, 400 MHz): δ0.83 (d, 6H), 1.60 (m, 3H), 2.24 (s, 3H), 2.27 (m, 2H), 2.54 (m, 2H), 3.11 (m, 2H), 6.74 (m, 1H), 7.02 (m, 1H), 7.14 (m, 1H)

MS (EI, m/z): 254/256 [M]$^+$.

Step B. 1-(6-Chloro-2-methyl-phenyl)-3-isobutyl-3,4,5,6-tetrahydropyrimidine-2(1H)-thione To a solution of the diamine of Step A (3.82 g) in dry chloroform (55 mL) was added dropwise at 0° C. under nitrogen triethylamine (4.18 mL) followed by thiophosgene (2.6 g). The mixture was stirred in the cold for 15 minutes and then at room temperature for 60 minutes. It was then diluted with water and after adjusting the pH to 8 with triethylamine, was extracted with dichloromethane. The combined extracts were washed with 20% aqueous sodium chloride, dried over anhydrous potassium carbonate and evaporated to dryness. The residue was flash chromatographed (on Merck-60 flash silica gel, 85:15 hexane-EtOAc) to provide 3.37 g of the title compound. Trituration and sonication with hexane and hexane-ether yielded an off-white solid (2.26 g, 51.1%), m.p. 119–121° C.

NMR (DMSO-$d_6$, 400 MHz): δ0.89 (d, 6H), 2.07–2.17 (m, 3H), 2.19 (s, 3H), 3.39 (t, 2H), 3.49 (t, 2H), 3.66–3.84 (m, 2H), 7.17 (m, 2H), 7.30 (m, 1H)

MS (+FAB, m/z): 297⁄299 [M+H]$^+$

Anal. Calcd for $C_{15}H_{21}ClN_2S$: C, 60.69; H, 7.13; N, 9.44. Found: C, 60.80; H, 6.94; N, 9.42.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula:

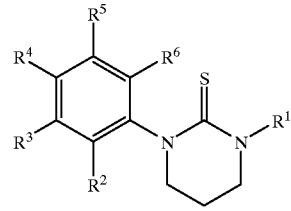

wherein:
   $R^1$ is, alkyl of 1–6 carbon atoms, cycloalkyl of 3–8 carbon atoms, alkenyl of 2–7 carbon atoms; an
   $R^2$, $R^3$, $R^4$, $R^5$, and $R^6$ are each, independently, hydrogen, halogen, or alkyl of 1–6 carbon atoms;
or a pharmaceutically acceptable salt thereof.

2. The compound of claim 1, wherein $R^1$ is methyl, ethyl, isopropyl or cyclobutyl; and $R^2$, $R^3$, $R^4$, $R^5$, and $R^6$ are each, independently, chlorine or methyl.

3. The compound of claim 1, which is 1-(4-chloro-2-methyl-phenyl)-3,4,5,6-tetrahydro-pyrimidine-2(1H)-thione.

4. The compound of claim 1, which is 1-(4-chloro-2-methyl-phenyl)-3-ethyl-3,4,5,6-tetrahydro-pyrimidine-2(1H)-thione.

5. The compound of claim 1, which is 1-(2,6-dimethyl-phenyl)-3,4,5,6-tetrahydro-pyrimidine-2(1H)-thione.

6. The compound of claim 1, which is 1-(5-chloro-2-methyl-phenyl)-3-ethyl-3,4,5,6-tetrahydro-pyrimidine-2(1H)-thione.

7. The compound of claim 1, which is 1-(5-chloro-2-methyl-phenyl)-3-isopropyl-3,4,5,6-tetrahydro-pyrimidine-2(1H)-thione.

8. The compound of claim 1, which is 1-(4-chloro-2-methyl-phenyl)-3-isopropyl-3,4,5,6-tetrahydro-pyrimidine-2(1H)-thione.

9. The compound of claim 1, which is 3-allyl-1-(5-chloro-2-methyl-phenyl)-3,4,5,6-tetrahydro-pyrimidine-2(1H)-thione.

10. The compound of claim 1, which is 1-(5-chloro-2-methyl-phenyl)-3-methyl-3,4,5,6-tetrahydro-pyrimidine-2(1H)-thione.

11. The compound of claim 1, which is 3-allyl-1-(4-chloro-2-methyl-phenyl)-3,4,5,6-tetrahydro-pyrimidine-2(1H)-thione.

12. The compound of claim 1, which is 1-(4-chloro-2-methyl-phenyl)-3-methyl-3,4,5,6-tetrahydro-pyrimidine-2(1H)-thione.

13. The compound of claim 1, which is 3-allyl-1-(6-chloro-2-methyl-phenyl)-3,4,5,6-tetrahydro-pyrimidine-2(1H)-thione.

14. The compound of claim 1, which is 1-(6-chloro-2-methyl-phenyl)-3-methyl-3,4,5,6-tetrahydro-pyrimidine-2(1H)-thione.

15. The compound of claim 1, which is 1-(5-chloro-2-methyl-phenyl)-3-isobutyl-3,4,5,6-tetrahydro-pyrimidine-2(1H)-thione.

16. The compound of claim 1, which is 1-(6-chloro-2-methyl-phenyl)-3-isopropyl-3,4,5,6-tetrahydro-pyrimidine-2(1H)-thione.

17. The compound of claim 1, which is 1-(6-chloro-2-methyl-phenyl)-3-ethyl-3,4,5,6-tetrahydro-pyrimidine-2(1H)-thione.

18. The compound of claim 1, which is 1-(4-chloro-2-methyl-phenyl)-3-isobutyl-3,4,5,6-tetrahydro-pyrimidine-2(1H)-thione.

19. The compound of claim 1, which is 1-(6-chloro-2-methyl-phenyl)-3-cyclobutyl-3,4,5,6-tetrahydro-pyrimidine-2(1H)-thione.

20. The compound of claim 1, which is 1-(5-chloro-2-methyl-phenyl)-3-cyclobutyl-3,4,5,6-tetrahydro-pyrimidine-2(1H)-thione.

21. The compound of claim 1, which is 1-(6-chloro-2-methyl-phenyl)-3-isobutyl-3,4,5,6-tetrahydro-pyrimidine-2(1H)-thione.

22. A method of treating atherosclerosis in a mammal in need thereof, which comprises administering to said mammal an anti-atherosclerotic effective amount of a compound of the structure:

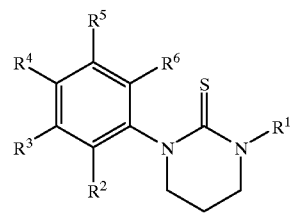

wherein:
$R^1$ is alkyl of 1–6 carbon atoms, cycloalkyl of 3–8 carbon atoms or alkenyl of 2–7 carbon atoms; and
$R^2$, $R^3$, $R^4$, $R^5$, and $R^6$ are each, independently, hydrogen, halogen or alkyl of 1–6 carbon atoms,
or a pharmaceutically acceptable salt thereof.

23. A pharmaceutical composition, which comprises a compound of the formula:

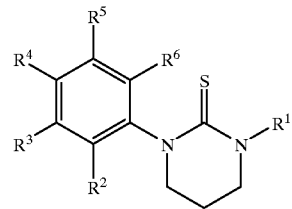

wherein:
$R^1$ is alkyl of 1–6 carbon atoms, cycloalkyl of 3–8 carbon atoms or alkenyl of 2–7 carbon atoms; and
$R^2$, $R^3$, $R^4$, $R^5$, and $R^6$ are each, independently, hydrogen, halogen or alkyl of 1–6 carbon atoms;
or a pharmaceutically acceptable salt thereof and a pharmaceutical carrier.

* * * * *